United States Patent [19]

Merianos et al.

[11] Patent Number: 5,130,124
[45] Date of Patent: Jul. 14, 1992

[54] STABILIZED, AQUEOUS, FILM-FORMING ANTIMICROBIAL COMPOSITIONS OF HYDROGEN PEROXIDE

[75] Inventors: John J. Merianos, Middletown; Robert P. Login, Oakland; Paul Garelick, South Plainfield, all of N.J.

[73] Assignee: ISP Investments Inc., Wilmington, Del.

[21] Appl. No.: 694,169

[22] Filed: May 1, 1991

[51] Int. Cl.$^5$ .................. A61K 7/135; A61K 7/20; A61K 33/40; A61K 31/79
[52] U.S. Cl. ............................ 424/53; 424/62; 424/616
[58] Field of Search .............. 424/62, 53, 80, 612-616

[56] References Cited

U.S. PATENT DOCUMENTS

| | | | |
|---|---|---|---|
| 3,898,032 | 8/1975 | Edman et al. | 514/772 |
| 3,906,091 | 9/1975 | Zviak et al. | 424/62 |
| 3,912,446 | 10/1975 | Zviak et al. | 424/62 |
| 4,200,432 | 4/1990 | Kalopissis et al. | 8/408 |
| 4,494,953 | 1/1985 | Bugaut et al. | 8/408 |
| 4,518,583 | 5/1985 | Gallina | 424/80 |
| 4,592,487 | 6/1986 | Simon et al. | 424/53 |
| 4,696,757 | 9/1987 | Blank et al. | 424/62 |
| 4,775,527 | 10/1988 | Bires et al. | 424/62 |
| 4,781,923 | 11/1988 | Pellico | 424/616 |
| 4,839,156 | 6/1989 | Ng et al. | 424/53 |
| 4,850,729 | 7/1989 | Kramer et al. | 252/106 |
| 4,895,721 | 1/1990 | Drucker | 424/53 |
| 5,008,106 | 4/1991 | Merianos et al. | 424/80 |

FOREIGN PATENT DOCUMENTS

| | | | |
|---|---|---|---|
| 60/32710 | 2/1985 | Japan | 424/62 |
| 61/158907 | 7/1986 | Japan | 424/616 |
| 224135 | 11/1924 | United Kingdom | 424/62 |
| 821726 | 10/1959 | United Kingdom | 424/62 |
| 1152860 | 5/1969 | United Kingdom | 424/616 |
| 1217971 | 1/1971 | United Kingdom | 424/62 |

OTHER PUBLICATIONS

Wacker-Chemie C.A. 71 #23006M (969) of Gt. Br. 1,152,860 (May 21, 1969).
Kashiwa K.K. C.A. 103 #112227A (1985) of JPN 6032710 (Feb. 19, 1985).

*Primary Examiner*—Shep K. Rose
*Attorney, Agent, or Firm*—Walter Katz; Marilyn J. Maue; Joshua J. Ward

[57] ABSTRACT

What is provided herein is a stabilized, aqueous, film-forming, antimicrobial composition of hydrogen peroxide. The active, oxygen-generating hydrogen peroxide component in the composition is stabilized in an aqueous-polyol solvent system of predetermined polarity containing PVP. In contrast, similar formulations without PVP experienced a loss of peroxide activity upon standing. Suitably, the composition herein includes about 1-20% by weight hydrogen peroxide, about 0.1-50% by weight PVP, and about 0.1-80% by weight of a polyol, the rest being water. Preferably, about 5-20% by weight of water is present in the composition. Additional solvents may be included therein, such as alcohols, ether oxides, esters, triglycerides of fatty acids, hydrocarbons, N-vinyl lactams, silicone oils, and polyether oligomers.

9 Claims, No Drawings

STABILIZED, AQUEOUS, FILM-FORMING ANTIMICROBIAL COMPOSITIONS OF HYDROGEN PEROXIDE

BACKGROUND OF THE INVENTION

1. Field of the Invention

This invention relates to a stabilized, aqueous film-forming, antimicrobial composition, and more particularly, to such composition comprising hydrogen peroxide ($H_2O_2$), polyvinylpyrrolidone (PVP), a polyol, and water.

2. Background of the Prior Art

Hydrogen peroxide is a well known antispectic which has been extensively employed in aqueous solution for the treatment of infectious processes in both human and veterinary topical therapy. The agent can be used in its original form after suitable dilution, or it can be derived from those solid compounds which form salts or additive compounds with hydrogen peroxide. Included among these are sodium perborate, sodium carbonate peroxide, sodium peroxyphosphate, urea peroxide, potassium persulfate, and others. When added to water, these compounds hydrolyze into hydrogen peroxide and the corresponding carrying salt.

Although extensively employed for treating all parts of the body, hydrogen peroxide has proved especially valuable for treating the mucous membranes of the oral cavity. Partly as a consequence of oxygen tissue metabolic and reparative requirements (by a mechanism which is not clearly understood), partly as a consequnce of its broad antibacterial effects against gram positive and gram negative cocci, bacillus and spirochetal forms as well as many varieties of yeasts and fungi, and partly because of its cleaning and hemostatic effects, hydrogen peroxide is extensively recommended and used for bacterial and viral infections and for tissue inflammations of non-microorganic origin.

The principal limitations of commonly used peroxide aqueous solutions, however, are their poor shelf stability caused by the decomposition of hydrogen peroxide into gaseous oxygen and water at room temperature, and the transitory contact of the active oxygenating agent with the affected tissue. In addition, when such compositions are formed of additive compounds with hydrogen peroxide, it is common to prepare the adduct composition before incorporating it into the desired composition.

The following U.S. Pat. Nos. are illustrative of the state of this art: 3,376,110; 3,480,557; 3,629,331; 3,657,413; 4,155,738; 4,302,441; 4,514,384; 4,518,583; 4,522,805; 4,528,180; 4,609,674; 4,826,681; 4,837,008; and 4,895,875.

However, these and other references of the prior art do not provide a stabilized, aqueous, film-forming antimicrobial composition of hydrogen peroxide which has an extended shelf-life with respect to decomposition into oxygen and water, an increased period of retention on tissues, and which can be formulated in situ from aqueous hydrogen peroxide, a stabilizing and film-forming agent, and a viscosity modifier.

Accordingly, it is among the objects of the present invention to provide an aqueous antimicrobial composition of hydrogen peroxide which has a stable shelf-life, is capable of being retained on oral tissue for extended periods of time, is a film-former on application to an infected tissue, and which can be formulated in situ from an aqueous hydrogen peroxide solution, a stabilizing, film-forming and complexing agent capable of complexing with hydrogen peroxide in a defined molar ratio, and a viscosity modifier in which the stabilizing agent can function effectively to provide the desired stabilized composition.

These and other objects and features of the invention will be made apparent from the following description thereof.

SUMMARY OF THE INVENTION

What is provided herein is a stabilized, aqueous, film-forming, antimicrobial composition of hydrogen peroxide. The active, oxygen-generating hydrogen peroxide component in the composition is stabilized in an aqueous-polyol solvent system of predetermined polarity containing PVP. In contrast, similar formulations, without PVP, experienced a loss of peroxide activity upon standing. Suitable, the composition includes about 1-20% by weight hydrogen peroxide, about 0.1-50% by weight PVP, and about 0.1-80% by weight of a polyol, the rest being water. Preferably, about 1-20% by weight of water is present in the composition. Additional solvents may be included therein, such as alcohols, ether oxides, esters, triglycerides of fatty acids, hydrocarbons, N-vinyl lactams, silicone oils, and polyether oligomers.

DETAILED DESCRIPTION OF THE INVENTION

It has been observed herein that aqueous hydrogen peroxide solutions can be stabilized by PVP in a predetermined solvent system of given polarity. In such formulations, the in situ formed $PVP-H_2O_2$ complex does not dissociate readily even after prolonged standing. Accordingly, stabilized, aqueous, film-forming antimicrobial compositions of hydrogen peroxide are provided which can be prepared economically from the respective individual components, as follows:

| COMPOSITION OF INVENTION | | | |
|---|---|---|---|
| | % by Weight | | |
| | Suitable | Preferred | Optimum |
| Essential Components | | | |
| 1) $H_2O_2$ (added as 30-70% aqueous solution) | 1-20 | 6-12 | 7.5 |
| 2) PVP (added as a K-15 to K-90, water soluble or water-insoluble powder) | 0.1-50 | 12-25 | 15 |
| 3) Polyol | 0.1-70 | 15-75 | 65 |
| 4) Water | 2.5-35 | 5-20 | 12.5 |
| Optional Components | | | |
| 1) Other solvents, e.g. alcohols, ether oxides, esters, triglycerides of fatty acids, hydrocarbons, N-alkyl lactams, silicone oils, polyether oligomers | 0-10 | 2-5 | 2.5 |
| 2) Wetting, emulsifying, surfactant and suspending agents | 0-3 | 1-2.5 | 1.5 |

The active hydrogen peroxide component of the composition of the invention provides the desired oxygenating action against microbes. Accordingly, the composition is effective as a wound dressing, mouthwash, in toothpaste, for the treatment of hemorrhoids, and in a contact lens sterilization solution.

The composition is prepared conveniently by mixing an aqueous solution of $H_2O_2$, PVP powder and a polyol solvent, optionally with an added solvent and adjuvant materials.

The invention will be illustrated by the following examples.

EXAMPLE 1

A. A composition of the invention was prepared from 14.1 g of a 70% aqueous solution of $H_2O_2$ (9.1 g $H_2O_2$), 42.5 g of PVP (soluble PVP-K-15, <1% water), 42.6 g of propylene glycol and 5 g of water. After 5 months at 40° C. in an oven closed off from air, the $H_2O_2$ content was analyzed at 9.5%.

B. A control formulation of 12.2% $H_2O_2$, 82.8 g propylene glycol and 5 g water was tested as above. At the end of 5 months at 40° C., the $H_2O_2$ content was only 1.1%.

EXAMPLE

A. A composition of the invention was prepared as in Example 1-A comprising 10.7 g $H_2O_2$, 40 g PVP, 39.3 g propylene glycol and 10 g water. Upon heating at 40° C. for 5 months, the $H_2O_2$ content analyzed 9.6%. B. A control formulation of 12.2 g $H_2O_2$, 77.8 g propylene glycol and 10 g water showed a drop to 3.5 g. $H_2O_2$ after a similar test period.

EXAMPLE 3

A. A formulation of 11.2 g $H_2O_2$, 35 g PVP, 38.8 g propylene glycol and 15 g water retained its peroxide content at a 9.9 g level after the same test period.

B. A control formulation of 12.0 g $H_2O_2$, 73.0 g propylene glycol and 15 g water experienced a decline to 6.6 g $H_2O_2$ under the same test conditions.

COMPARATIVE
EXAMPLE 4

A. A formulation of 12.8 g $H_2O_2$, 42.5 g PVP, 39.7 g ethanol and 5 g water had a 11.9 g $H_2O_2$ level after 5 months at 40° C.

B. A control formulation of 12.9 g $H_2O_2$, 82.1 g ethanol and 5 g of water had a 10.1 g $H_2O_2$ level after the same treatment as above.

COMPARATIVE
EXAMPLE 5

A. A formulation of 12.2 g $H_2O_2$, 42.5 g PVP, 35.3 g ethanol and 5 g water had a $H_2O_2$ level of 12.0 after a similar treatment as above.

B. A control formulation of 13.2 g $H_2O_2$, 76.8 g ethanol and 10 g water showed a $H_2O_2$ content of 10.3 after the test period.

COMPARATIVE
EXAMPLE 6

A. 11.6 g of $H_2O_2$, 35 g of PVP, 33.4 g of ethanol and 20 g of water retained its $H_2O_2$ activity at 11.1 g after the test period.

B. 12.4 g of $H_2O_2$, 67.6 g of ethanol and 20 g of water showed a $H_2O_2$ level of 11.7 g after the test period.

While the invention has been described with particular reference to certain embodiments thereof, it will be understood that changes and modifications may be made which are within the skill of the art. Accordingly, it is intended to be bound only by the following claims, in which:

What is claimed is:

1. A stabilized, aqueous, film-forming, antimicrobial composition of hydrogen peroxide consisting essentially of (a) about 1-20% by weight of hydrogen peroxide added as a 30-70% by weight aqueous solution; (b) about 0.1-50% by weight of a water soluble or water-insoluble polyvinylpyrrolidone having a K-value ranging from K-15 to K-90; (c) about 0.1-80% by weight of a polyol selected from the group consisting of propylene glycol, glycerol and polyethylene glycol; and (d) about 2.5-35% by weight of water.

2. A composition according to claim 1 which also includes about 2-10% by weight of one or more of a solvent selected from an alcohol, ether oxide, ester, triglycerides of fatty acids, hydrocarbon, N-alkyl lactam, silicone oil, polyether oligomer, and about 1-3% of one or more of an adjuvant selected from a wetting agent, emulsifying agent and suspending agent.

3. A composition according to claim 1 wherein (a) is about 6-12%; (b) is about 12-25%; (c) is about 15-75%; and (d) is about 5-20%.

4. A composition according to claim 1 wherein (a) is about 7.5%; (b) is about 15%; (c) is about 65%; and (d) is about 12.5%.

5. A wound dressing, mouthwash, toothpaste, antihemorrhoid, or contact lens sterilization formulation which includes the composition of claim 1.

6. A composition according to claim 1 wherein said polyol is propylene glycol.

7. A composition according to claim 1 wherein said polyol is glycerol.

8. A composition according to claim 1 wherein said polyol is polyethylene glycol.

9. A composition according to claim 1 wherein about 2-10% ethanol is included therein.

* * * * *